United States Patent [19]

Norton

[11] 4,218,570

[45] Aug. 19, 1980

[54] METHOD FOR PURIFICATION OF ORGANIC REACTION PRODUCTS

[75] Inventor: Richard V. Norton, Dublin, Ohio

[73] Assignee: Ashland Oil, Inc., Ashland, Ky.

[21] Appl. No.: 13,096

[22] Filed: Feb. 21, 1979

[51] Int. Cl.$^2$ .............................................. C07C 13/28
[52] U.S. Cl. ....................................... 585/23; 585/362
[58] Field of Search ................................... 585/23, 362

[56] References Cited

U.S. PATENT DOCUMENTS

| | | | |
|---|---|---|---|
| 4,094,916 | 6/1978 | Thomas | 585/362 |
| 4,094,917 | 6/1978 | Thomas | 585/362 |

Primary Examiner—Veronica O'Keefe

[57] ABSTRACT

Liquid organic reaction products prepared in the presence of homogeneous iron catalyst values are contacted with a strong Lewis acid to effect removal of said values as inorganic precipitates.

6 Claims, No Drawings

METHOD FOR PURIFICATION OF ORGANIC REACTION PRODUCTS

BACKGROUND OF THE INVENTION

1. Field of the Invention

This invention relates to a method for the purification of homogeneous iron complex catalyzed organic reaction products.

2. Description of the Prior Art

Homogeneous iron catalysts; i.e., organic soluble iron in the form of covalently bonded complexes thereof, are widely used in the chemical industry for catalyzing a variety of reactions. Although iron complexes of this type are used in relatively small amounts to effect catalysis, they must be removed if not only because of the intense objectionable coloration these species impart to the final product and because their presence imparts chemical instability to the products. Moreover, many of the indicated products are chemical intermediates whose specifications and end use requirements frequently exclude the presence of all but trace amounts of iron.

In a number of instances the organic product of the catalysis reaction can be readily distilled to accomplish purification thereof. On the other hand there are likewise numerous instances where a distillation operation does not represent a viable expedient due to the relatively high vapor pressure of the homogeneous iron catalyst and the resultant codistillate. Also, in some situations it is not feasible to accomplish the degree of purification required by distillation since the organic products are temperature unstable and frequently cannot survive the long temperature exposures required for fractional distillation.

Heretofore, it has been proposed to rid reaction products of their spent organic soluble iron catalyst values by the addition of formic acid and hydrogen proxide so as to generate performic acid in situ. The latter reacts with the iron impurities to form water-soluble species thereof which can be readily removed by a convenient washing operation. This prior art method is effective but suffers because the relatively large amount of performic acid involved in high volume commercial production operations poses potentially hazardous conditions due to the thermodynamic instability of this reactant.

SUMMARY OF THE INVENTION

In accordance with the present invention a facile method is provided for eliminating iron catalyst values from organic reaction products wherein the catalyst exists as an organic soluble complex. The improved method involves intimately contacting the resultant reaction mixture with a strong Lewis acid salt in an amount effective for substantially completely converting the catalyst to inorganic precipitates.

DESCRIPTION OF THE INVENTION

As indicated previously, homogeneous iron catalysts find widespread utilization in the chemical industry. Representative general applications of this type include the following unit chemical operations: hydrogenation or reduction; hydrosilylation; dehydrogenation or dehydrosulfuration; deoxygenation; and isomerization. A specific but important singularly effective use of homogeneous iron systems, however, resides in the production of a polycyclic hydrocarbon having exceptionally high volumetric energy (BTU/gal) designed for fueling volume limited missile systems. The present invention will accordingly be illustrated in context of such an embodiment.

Particularly exemplary of the aforesaid high energy fuels is the hydrogenated product of an isomeric mixture of norboradiene, (bicyclo (2.2.1.) heptadiene) dimers as described in U.S. Pat. Nos. 3,282,663 and 3,377,398. The dimers are obtained by contacting norboradiene with a catalyst in the form of an iron-ligand complex at a temperature in excess of about 140° C. A variety of ligands are applicable for complexing with iron of which acetylacetonate is particularly suitable. In addition to the iron catalyst, it is preferred to employ an organic soluble aluminum compound; e.g., a trialkyl aluminum, as an activator. Following dimerization the resultant product is hydrogenated.

Dimerized products prepared as aforesaid contain in the order of about 1% by weight of the iron complex catalyst. Following distillation, which is customarily observed in the production of such fuels, the distilled product ordinarily contains from 100-200 parts per million iron and on occasion contains 300-500 ppm iron if more catalyst had to be used to obtain faster dimerization kinetics.

In accordance with this invention, the distilled product is contacted with a strong Lewis acid salt at ambient temperature or moderately in excess thereof for a period of time, usually not longer than about 30 minutes. The process is also workable with undistilled hydrogenated dimer but the very high level of iron in crude material 0.5 to 1.5% makes an initial distillation step desirable. Applicable Lewis acid salts include the halides of aluminum, boron, zinc and tin. The preferred treating agent is anhydrous aluminum trichloride (solids) in fine powder. The dosage for effecting purification depends on the iron content of the product. For example, 5-10 weight percent of aluminum chloride on the total product is ample for the substantially complete elimination of iron to 5 ppm wherein the initial contaminants amounted to 30-200 parts per million. Where the contamination level exceeds 200 parts per million an amount of the treating agent in the order of 15% is desirably indicated. However, the use of conventional trickle bed or packed bed percolating bed treatments are reasonable alternatives and represent a continuous process. Successive treatments with appropriate dosages are applicable at a high level of contamination or where it is desirable to attain a nil iron content.

The following working example is set forth as illustrative of the invention.

EXAMPLE I

To a suitable vessel equipped with an agitator were charged 250 parts by weight of a hydrogenated norbornadiene dimer prepared in the manner outlined above. The crude hydrogenated dimer product exhibited a deep orange color (Saybolt color #1) and contain about 200 parts per million residual iron. With stirring, 10 parts by weight aluminum chloride were added. Stirring was continued for 30 minutes at ambient temperature whereupon the accummulated sludge was allowed to settle and the clarified product then decanted. Filtration of the product through filter paper provided a clear (almost colorless Saybolt color #24) filtrate containing less than 20 parts per million iron.

What is claimed is:

1. In a method for removing catalyst values from a liquid organic reaction product in which said catalyst consists essentially of an organic soluble iron-ligand complex; the improvement comprising contacting said organic reaction product with a Lewis acid in the form of a halide salt of a metal selected from the group consisting of aluminum, boron, zinc and tin, to effect precipitation of said complex.

2. The improvement in accordance with claim 1 wherein the Lewis acid is aluminum chloride.

3. The improvement in accordance with claim 1 wherein said organic reaction product is that provided by the dimerization of norbornadiene.

4. The improvement in accordance with claim 3 wherein said organic reaction product is hydrogenated dimerized norbornadiene.

5. The improvement in accordance with claim 4 wherein said ligand is acetylacetonate.

6. The improvement in accordance with claim 5 wherein said Lewis acid is aluminum chloride.

* * * * *